US00PP29567P2

(12) United States Plant Patent
O'Connell

(10) Patent No.: US PP29,567 P2
(45) Date of Patent: Jul. 31, 2018

(54) ***AEONIUM* 'MADEIRA ROSE'**

(50) Latin Name: *Aeonium hybrida*
Varietal Denomination: Madeira Rose

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/731,164

(22) Filed: Apr. 26, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Aeonium* cultivar named 'Madeira Rose' is disclosed, characterized by concentric olive green rosettes with a bronze blush. Plants grow quickly, forming rings of even, concentric offsets at a distinctively young age. Due to abundant and early offsetting, plants can quickly fill a variety of commercial pot sizes, while maintaining an attractive compact habit. Mature plants are medium sized, growing to approximately 12 to 15 inches in height and 24 to 30 inches in diameter. Plants are observed tolerant of sunny and hot Summer conditions without requiring shade or protection. *Aeonium* is, typically produced as a container plant for the patio or for landscape use.

1 Drawing Sheet

Latin name of the genus and species: *Aeonium hybrida.*
Variety denomination: 'MADEIRA ROSE'.

BACKGROUND OF THE INVENTION

The new cultivar, *Aeonium* 'Madeira Rose', was found by the inventor, Renee O'Connell, as the result of a crossing made March 2012 as part of a planned breeding program. The seed parent variety is the unpatented proprietary variety referred to as *Aeonium hybrida* 'BB II'. The pollen parent is the unpatented variety *Aeonium hybrida* 'Coronado Lime'. *Aeonium* 'Madeira Rose' was selected by the inventor, Renee O Connell, in April of 2013 from a group of seedlings resulting from the 2012 crossing, at a commercial greenhouse in Vista. Calif.

Asexual reproduction of the new cultivar 'Madeira Rose' was first performed in Vista, Calif., at a commercial greenhouse, by vegetative off-sets in October of 2013. 'Madeira Rose' has since produced multiple generations and has shown that the unique features of this cultivar are stable and reproduced true to type.

SUMMARY OF THE INVENTION

The cultivar 'MADEIRA ROSE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MADEIRA ROSE' These characteristics in combination distinguish 'MADEIRA ROSE' as a new and distinct *Aeonium* cultivar:

1. *Aeonium* 'Madeira Rose' produces very concentric olive green rosettes which can blush bronze in strong light, giving a two-toned appearance to the plant.
2. *Aeonium* 'Madeira Rose' freely produces rings of offsets at an early age, quickly producing an attractive cluster.
3. *Aeonium* 'Madeira Rose', due to the profuse production of offsets, quickly fills a production pot, thereby reducing production time.
4. *Aeonium* 'Madeira Rose' typically grows to 12" to 15" in height, continuing to spread laterally to 24" to 30" or more in diameter.
5. *Aeonium* 'Madeira Rose' is fast growing, quickly filling larger pot sizes, thereby reducing crop time in a commercial setting.

PARENTAL COMPARISON

Plants of the new cultivar 'MADEIRA ROSE' are similar to plants of the seed parent in most horticultural characteristics, however, plants of the new cultivar 'MADEIRA ROSE' differ in the following;

1. *Aeonium* 'Madeira Rose' differs from *Aeonium* 'BB II' in that it freely produces rings or tiers of offsets, beginning at an early age, but continuing as it grows, whereas the seed parent *Aeonium* 'BB II' produces offsets as well, but far less and does not produce the multiple "rings" of offsets.
2. *Aeonium* 'Madeira Rose' blushes a darker copper color than does *Aeonium* 'BB II'.
3. *Aeonium* 'Madeira Rose' forms clusters of rosettes that grow to 12" to 15" tall by 24" or more inches in diameter, whereas *Aeonium* 'BB II' does not.
4. The green color of *Aeonium* 'BB II' is darker than the green color of *Aeonium* 'Madeira Rose'.

Plants of the new cultivar 'MADEIRA ROSE' are similar to plants of the pollen parent in most horticultural characteristics, however, plants of the new cultivar 'MADEIRA ROSE' differ in the following;

1. *Aeonium* 'Madeira Rose' forms rosettes of olive leaves with copper to bronze overtones, whereas the pollen parent *Aeonium* 'Coronado Lime' produces lime green rosettes.
2. *Aeonium* 'Madeira Rose' forms clusters of dense tiers of offsets on a mid-sized plant, whereas *Aeonium* 'Coronado Lime' tends to be a shorter plant.
3. *Aeonium* 'Madeira Rose' differs from *Aeonium* 'Coronado Lime' in that it freely produces rings or tiers of offsets, beginning at an early age, but continuing as it grows, whereas the seed parent *Aeonium* 'Coronado Lime' produces offsets as well, but usually a single ring with more offsets, with an occasional offset as it ages.
4. *Aeonium* 'Madeira Rose' produces a more concentric plant than *Aeonium* 'Coronado Lime'.
5. *Aeonium* 'Madeira Rose' performs better in full sun in the landscape than does *Aeonium* 'Coronado', which only performs well with afternoon shade, particularly in the hot summer months.

COMMERCIAL COMPARISON

Plants of the new cultivar 'MADEIRA ROSE' are comparable to the unpatented, commercial variety *Aeonium* 'Zwartkin'. The two *Aeonium* varieties are similar in most horticultural characteristics; however, the new variety 'MADEIRA ROSE' differs in the following:

1. *Aeonium* 'Madeira Rose' forms clusters, ringed with several tiers of offsets, whereas *Aeonium* 'Zwartkin', although it does offset, produces less offsets, and does not produce the multiple tiers of lateral offsets.
2. *Aeonium* 'Madeira Rose' displays foliage colors of olive-apple green, with copper or bronze secondary color, whereas *Aeonium* 'Zwartkin' produces dark foliage colors, much like *Aeonium* 'Zwartkopf'.
3. Plants of *Aeonium* 'Madeira Rose' are 15" or more in height, with a lateral dimension of 24" to 30" in width, whereas plants of *Aeonium* 'Zwartkin' are 10" to 12" in height, and 12" to 15" in diameter.
4. *Aeonium* 'Madeira Rose' performs well in the landscape during the warmer Summer months, whereas *Aeonium* 'Zwartkin' requires shade protection during the warmer Summer months.

Plants of the new cultivar 'MADEIRA ROSE' can also be comparable to the unpatented commercial variety *Aeonium* 'Party Platter'. The two *Aeonium* varieties are similar in most horticultural characteristics; however, the new variety 'MADEIRA ROSE' differs in the following:

1. *Aeonium* 'Madeira Rose' forms rosettes of rich olive green, with copper points and at times blushed copper, whereas *Aeonium* 'Party Platter' forms rosettes of lime green.
2. The leaves of *Aeonium* 'Madeira Rose' are shiny whereas those of *Aeonium* 'Party Platter' are matte in texture.
3. *Aeonium* 'Madeira Rose' forms concentric rosettes, ringed with several tiers of offsets, whereas *Aeonium* 'Party Platter' forms many offsets, but the way in which they emerge causes the plant to look unbalanced, and for this reason, does not have the aesthetic appeal of a specimen of *Aeonium* 'Madeira Rose'.
4. *Aeonium* 'Madeira Rose' forms specimens at least 15" in height by 24" to 30" in diameter, whereas *Aeonium* 'Party Platter' forms lower growing specimens,

BRIEF DESCRIPTION OF THE PHOTOGRAPH

The accompanying photograph illustrates in full color a typical of plant of *Aeonium* 'Madeira Rose' grown in a shadehouse in Vista, Calif. at a light intensity of approximately 2500 to 3500 fc.

Age of the plant photographed is approximately 10 months from a rooted plantlet. The photograph was taken using conventional techniques and although colors may appear different from actual colors due to light reflectance it is as accurate as possible by conventional photographic techniques. All photographs provided by the breeder.

DETAILED BOTANICAL DESCRIPTION

In the following description, color references are made to The Royal Horticultural. Society Colour Chart, 2007, except where general terms of ordinary dictionary significance are used. The following observations and measurements describe 'Madeira Rose' plants in a commercial shade house in Vista, Calif. Temperatures ranged from approximately 1° C. to 38° C. night and day. No artificial light, photoperiodic treatments or chemical treatments were given to the plants. Natural light conditions were approximately 2500 to 3500 fc of light. Measurements and numerical values represent averages of typical plant types.

Botanical classification: *Aeonium hybrida* 'MADEIRA ROSE'.

PROPAGATION

Type of propagation typically used: Vegetative offsets.

Time to initiate roots: About 18 days at approximately 24° C.

Root description: Fibrous, brown, not accurately measured with a color chart.

PLANT

Age of plant described: Approximately 4 months.

Container size of the plant described: 1 gallon.

Growth habit: Upright, caulescent, with a terminal rosette, very freely offsetting. Tight, somewhat flattened rosette.

Height: Approximately 15 cm to top of highest leaf.

Plant spread: 32 cm.

Growth rate: Moderately fast.

Branching characteristics: Freely offsetting.

Rosettes per plant: Average range 10 to 14.

FOLIAGE

Leaf:

*Arrangement.*—Rosulate.

*Average length.*—Outer rosette mature leaf approximately 10 cm. Inner rosette mature leaf approximately 5 cm.

*Average width.*—3.0 cm.

*Width at base.*—1.1 cm.

*Shape of blade.*—Spatulate.

*Apex.*—Mucronate and blunt rounded.

*Base.*—Cuneate.

*Margin.*—Finely ciliate.

*Texture of top surface*.—Glabrous.
*Texture of bottom surface*.—Glabrous.
*Appearance of top surface*.—Glossy.
*Appearance of bottom surface*.—Glossy.
*Quantity of leaves per rosette*.—Average range 40 to 60.
*Color*.—Young foliage upper side: Base 143C. Mid-section near Greyed-Purple N186B. Apical margin 187B. Young foliage, under side: Near RHS Green 138B, flushed N186B near top, apical margin 187B. Base Yellow-Green 144D. Mature foliage upper side: Near RHS Green 137C. Base Yellow-Green 144D, lightly flushed 187D. Uppermost section flushed N186C. Apical margin 187B. Mature foliage, under side: Near RHS Green 138A. Base Green 138D, flushed 187D. Apical margin 186C.
*Venation*.—There is no visual appearance of venation.

FLOWER

Flowering not observed to date.

REPRODUCTIVE ORGANS

Flowering not observed to date.

OTHER CHARACTERISTICS

Fruits and seeds: Plant has not flowered or produced fruits and seeds to date.
Temperature tolerance: Tolerates temperatures from approximately −2 degrees C. to 40 degrees C.
Disease/pest resistance: Displays the same disease and pest resistance of any other comparable *Aeonium*.
Drought tolerance: Tolerates at least 3 weeks of high temperatures without supplemental water, showing no serious damage to plant.

What is claimed is:

1. A new and distinct cultivar of *Aeonium* plant named 'MADEIRA ROSE' as herein illustrated and described.

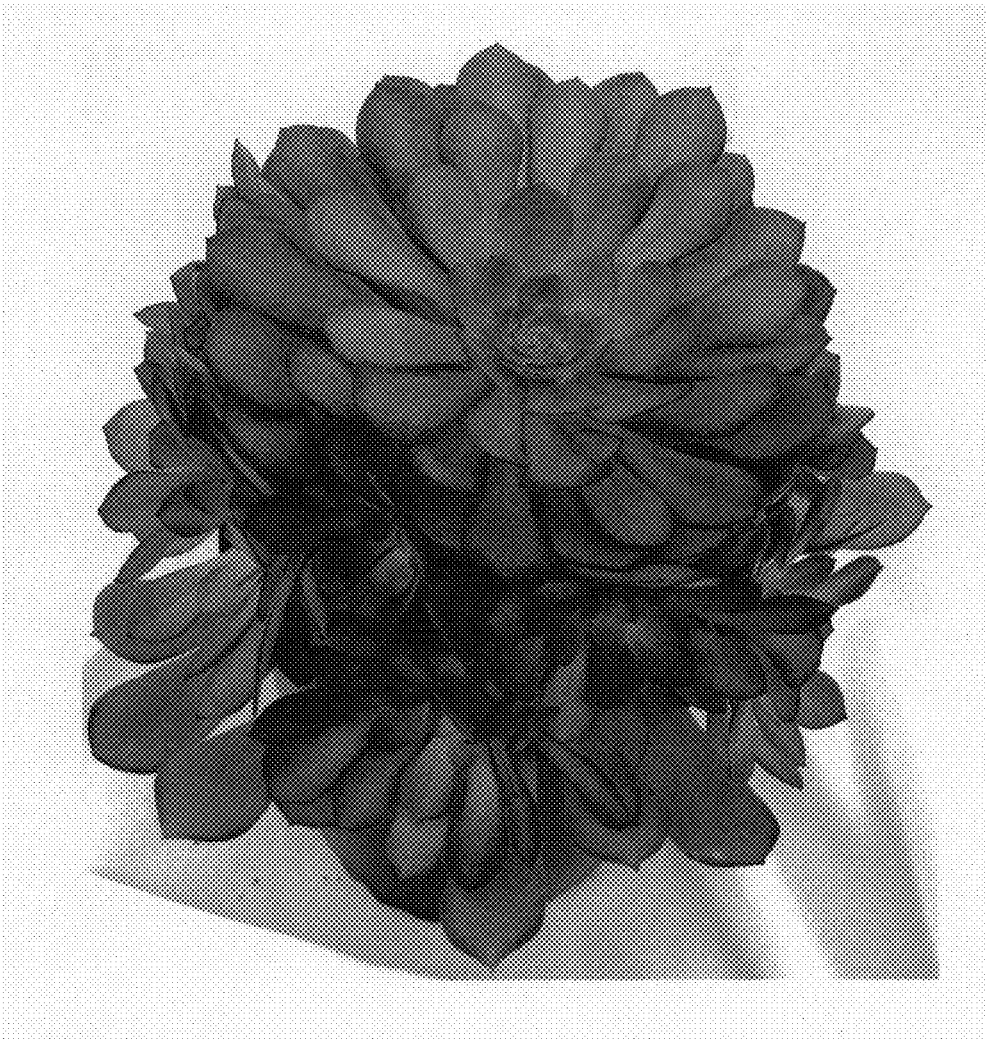

* * * * *